(12) United States Patent
Stähle et al.

(10) Patent No.: US 6,521,646 B1
(45) Date of Patent: Feb. 18, 2003

(54) DIBENZOAZULENE DERIVATIVES FOR TREATING THROMBOSIS, OSTEOPOROSIS, ARTERIOSCLEROSIS

(75) Inventors: Wolfgang Stähle, Ingelheim (DE); Rudolf Gottschlich, Reinheim (DE); Simon Goodman, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/958,812

(22) PCT Filed: Apr. 1, 2000

(86) PCT No.: PCT/EP00/02925

§ 371 (c)(1),
(2), (4) Date: Oct. 15, 2001

(87) PCT Pub. No.: WO00/63178

PCT Pub. Date: Oct. 26, 2000

(30) Foreign Application Priority Data

Apr. 14, 1999 (DE) .......................................... 199 16 837

(51) Int. Cl.⁷ ..................... A61K 31/44; C07D 213/00; C07C 65/26; C07C 69/76

(52) U.S. Cl. ..................... 514/352; 514/256; 514/275; 514/510; 514/564; 514/569; 560/21; 560/55; 562/435; 562/466; 546/285

(58) Field of Search .............................. 560/21, 35, 37, 560/55; 562/435, 440, 466; 514/256, 275, 352, 510, 564, 569; 546/285

(56) References Cited

U.S. PATENT DOCUMENTS 3,795,709 A * 3/1974 Frey et al.
6,069,158 A * 5/2000 Miller et al.

* cited by examiner

*Primary Examiner*—Sreeni Padmanabhan
*Assistant Examiner*—Paul A. Zucker
(74) *Attorney, Agent, or Firm*—Millen, White, Zelano & Branigan, P.C.

(57) ABSTRACT

Compounds of the formula (I) and their physiologically acceptable salts and solvates are useful as integrin-inhibiting substances. They are especially useful in the prophylaxis and treatment of cardiovascular disorders, of thrombosis, cardiac infarction, coronary heart diseases, arteriosclerosis, osteoporosis, in pathological conditions that are caused or propagated by angiogenesis and in tumor therapy.

21 Claims, No Drawings

DIBENZOAZULENE DERIVATIVES FOR TREATING THROMBOSIS, OSTEOPOROSIS, ARTERIOSCLEROSIS

This application is a 371 of PCT/EP00/02925 filed Apr. 1, 2000.

The invention relates to compounds of the formula I

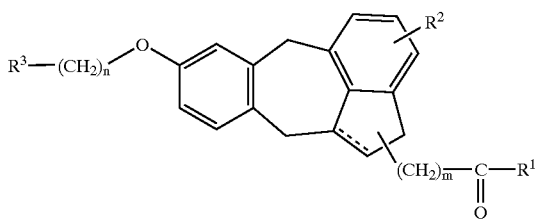

in which $R^1$ is $OR^4$, $NHR^4$ or $NA''_2$, $R^2$ is H, Hal, $NO_2$, $NHR^4$, $NA''_2$, $OR^4$, $SO_3R^4$, $SO_2R^4$ or $SR^4$, $R^3$ is $NH_2$, $H_2N$—C(=NH) or $H_2N$—(C=NH)—NH, where the primary amino groups can also be provided with conventional amino protective groups, or $R^5$—NH—, $R^4$ is H, A, Ar or Aralk, $R^5$ is a mono- or binuclear heterocycle having 1 to 4 N, O and/or S atoms, which can be unsubstituted or mono-, di- or trisubstituted by Hal, A", —CO—A', OA', CN, COOA', $CONH_2$, $NO_2$, =NH or =O, A is alkyl having 1–15 C atoms or cycloalkyl having 3–15 C atoms, which is unsubstituted or mono-, di- or trisubstituted by $R^6$, and in which one, two or three methylene groups can be replaced by N, O and/or S $R^6$ is Hal, $NO_2$, NHA', $NA''_2$, OA', phenoxy, CO—A', $SO_3A'$, CN, NHCOA', COOA', $CONA'_2$ or $SO_2A'$, A' is H or alkyl having 1–6 C atoms, A" is alkyl having 1–6 C atoms, Ar is a mono- or binuclear aromatic ring system, which is unsubstituted or mono-, di- or trisubstituted by alkyl having 1–6 C atoms and/or an $R^6$-substituted mono- or binuclear aromatic ring system having 0, 1, 2, 3 or 4 N, O and/or S atoms, Aralk is aralkylene having 7–14 C atoms, which is unsubstituted or mono-, di- or trisubstituted by $R^6$ and in which one, two or three methylene groups can be replaced by N, O and/or S, Hal is F, Cl, Br or I, m, n in each case independently of one another are 0, 1, 2, 3 or 4, and their physiologically acceptable salts and solvates.

Similar compounds are disclosed, for example, in WO 97/01540.

The invention is based on the object of finding novel compounds having valuable properties, in particular those which can be used for the production of medicaments.

It has been found that the compounds of the formula I and their salts and solvates have very valuable pharmacological properties, together with good tolerability. They act especially as integrin inhibitors, where they particularly inhibit the interactions of the $\alpha_v$ integrin receptors with ligands.

The compounds show particular activity in the case of the integrins $\alpha_v\beta_3$ and $\alpha_v\beta_5$. The compounds are very particularly active as adhesion receptor antagonists for the vitronectin receptor $\alpha_v\beta_3$.

This action can be demonstrated, for example, according to the method which is described by J. W. Smith et al. in J. Biol. Chem. 265, 11008–11013 and 12267–12271 (1990). In Curr. Opin. Cell. Biol. 5, 864 (1993), B. Felding-Habermann and D. A. Cheresh describe the importance of the integrins as adhesion receptors for very different phenomena and syndromes, especially with respect to the vitronectin receptor $\alpha_v\beta_3$.

The dependence of the formation of angiogenesis on the interaction between vascular integrins and extracellular matrix proteins is described by P. C. Brooks, R. A. Clark and D. A. Cheresh in Science 264, 569–71 (1994).

The possibility of inhibition of this interaction and thus of the initiation of apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157–64 (1994).

The experimental proof that the compounds according to the invention also prevent the attachment of living cells to the corresponding matrix proteins, and accordingly also the attachment of tumour cells to matrix proteins, can be furnished in a cell adhesion test which is carried out analogously to the method of F. Mitjans et al., J. Cell Science 108, 2825–2838 (1995).

In J. Clin. Invest. 96, 1815–1822 (1995), P. C. Brooks et al. describe $\alpha_v\beta_3$ antagonists for the control of cancer and for the treatment of tumour-induced angiogenic diseases. The compounds of the formula I according to the invention can therefore be employed as pharmaceutical active compounds, in particular for the treatment of oncoses, osteoporosis, osteolytic disorders and for the suppression of angiogenesis.

Compounds of the formula I which block the interaction of integrin receptors and ligands, such as, for example, of fibrinogen on the fibrinogen receptor (glycoprotein IIb/IIIa), prevent, as GPIIb/IIIa antagonists, the spread of tumour cells by metastasis. This is confirmed by the following observations: The spread of tumour cells from a local tumour into the vascular system takes place through the formation of microaggregates (microthrombi) by interaction of the tumour cells with blood platelets. The tumour cells are screened by protection in the microaggregate and are not recognized by the cells of the immune system. The microaggregates can fix themselves to vessel walls, as a result of which further penetration of tumour cells into the tissue is facilitated. Since the formation of microthrombi by fibrinogen binding to the fibrinogen receptors is mediated on activated blood platelets, the GPIIa/IIIb antagonists can be regarded as effective metastasis inhibitors.

Besides the binding of fibrinogen, fibronectin and the von Willebrand factor to the fibrinogen receptor of the blood platelets, compounds of the formula I also inhibit the binding of further adhesive proteins, such as vitronectin, collagen and laminin, to the corresponding receptors on the surface of various cell types. In particular, they prevent the formation of blood platelet thrombi and can therefore be employed for the treatment of thromboses, apoplexy, cardiac infarct, inflammation and arteriosclerosis.

The properties of the compounds can also be demonstrated according to methods which are described in EP-A1-0 462 960. The inhibition of fibrinogen binding to the fibrinogen receptor can be detected by the method which is indicated in EP-A1-0 381 033.

The platelet aggregation-inhibiting action can be demonstrated in vitro according to the method of Born (Nature 4832, 927–929, 1962).

The invention accordingly relates to the compounds of the formula I according to claim 1 and their physiologically acceptable salts and solvates as GPIIb/IIIa antagonists for the control of thromboses, cardiac infarct, coronary heart disorders and arteriosclerosis.

The invention furthermore relates to the compounds of the formula I according to claim 1 and their physiologically acceptable salts and solvates for the production of a medicament for use as an integrin inhibitor.

The invention relates in particular to compounds of the formula I according to claim 1 and their acceptable salts and solvates for the production of a medicament for controlling pathologically angiogenic disorders, tumours, osteoporosis, inflammation and infections.

The compounds of the formula I can be employed as pharmaceutical active compounds in human and veterinary medicine, for the prophylaxis and/or therapy of thrombosis, myocardial infarct, arteriosclerosis, inflammation, apoplexy, angina pectoris, oncoses, osteolytic diseases such as osteoporosis, pathologically angiogenic diseases such as, for example, inflammation, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, viral infection, bacterial infection, fungal infection, in acute kidney failure and in wound healing for assisting the healing process.

The compounds of the formula I can be employed as antimicrobially active substances in operations where biomaterials, implants, catheters or heart pacemakers are used. They have an antiseptic action here. The efficacy of the antimicrobial activity can be demonstrated by the process described by P. Valentin-Weigund et al., in Infection and Immunity, 2851–2855 (1988).

The invention further relates to a process for the preparation of compounds of the formula I according to claim 1, and of their salts and solvates, characterized in that a) a compound of the formula I is set free from one of its functional derivatives by treating with a solvolysing or hydrogenolysing agent, or b) a radical $R^1$, $R^2$ and/or $R^3$ is converted into another radical $R^1$, $R^2$ and/or $R^3$, by, for example, i) converting an amino group into a guanidino group by reaction with an amidinating agent,
ii) hydrolysing an ester,
iii) reducing a carboxylic acid to an alcohol,
iv) converting a hydroxyamidine into an amidine by hydrogenation and/or converting a base or acid of the formula I into one of its salts.

The compounds of the formula I have at least one chiral centre and can therefore occur in a number of stereoisomeric forms. All these forms (e.g. D and L forms) and their mixtures (e.g. the DL forms) are included in the formula I.

Also included in the compounds according to the invention are so-called prodrug derivatives, i.e. compounds of the formula I modified with, for example, alkyl or acyl groups, sugars or oligopeptides, which are rapidly cleaved in the body to give the active compounds according to the invention.

Solvates of the compounds are also included in the compounds according to the invention. These are understood to be addition compounds with, for example, water (hydrates) or alcohols such as methanol or ethanol.

The abbreviations mentioned above and below stand for:

| | |
|---|---|
| Ac | acetyl |
| BCC | tert-butoxycarbonyl |
| CBZ or Z | benzyloxycarbonyl |
| DCCI | dicyclohexylcarbodiimide |
| DBU | 1,8-diazabicyclo[5.4.0]undec-7-ene |
| DMF | dimethylformamide |
| DOPA | (3,4-dihydroxyphenyl)alanine |
| DPFN | 3,5-dimethylpyrazole-1-formamidinium nitrate |
| DMAP | dimethylaminopyridine |
| EDCI | N-ethyl-N,N'-(dimethylaminopropyl)carbodiimide |
| Et | ethyl |
| Fmoc | 9-fluorenylmethoxycarbonyl |
| HOBt | 1-hydroxybenzotriazole |
| Me | methyl |
| MTB ether | methyl tert-butyl ether |
| Mtr | 4-methoxy-2,3,6-trimethylphenylsulfonyl |
| HCNSu | N-hydroxysuccinimide |
| Np | neopentyl |
| CBn | benzyl ester |
| OBut | tert-butyl ester |
| Oct | octanoyl |
| OMe | methyl ester |
| OEt | ethyl ester |
| Orn | ornithine |
| POA | phenoxyacetyl |
| TBTU | O-(benzotriazol-1-yl)-N,N,N,N-tetramethyluronium tetrafluoroborate |
| TFA | trifluoroacetic acid |
| pTSS salt | para-toluenesultonic acid salt |
| Trt | trityl (triphenylmethyl) |
| Z or CBZ | benzyloxycarbonyl |

It is true for the whole invention that all radicals which occur a number of times can be identical or different, i.e. are independent of one another.

Formula I below

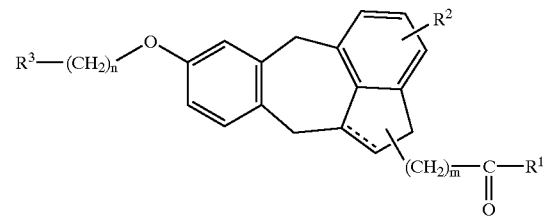

is

I'

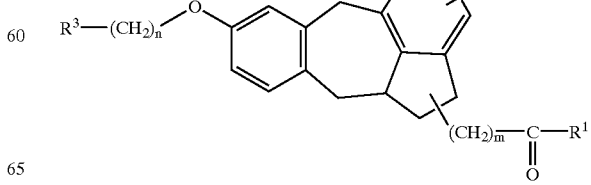

or

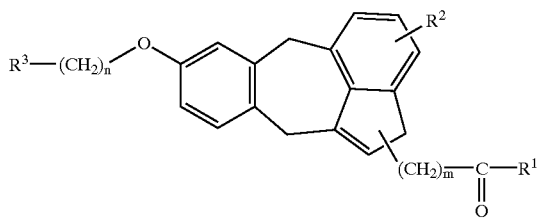

i.e. formula I includes those compounds of the formulae I' and I", which have a single or a double bond between C-1 and C-11a.

Alkyl is preferably methyl, ethyl, propyl, isopropyl, butyl, isobutyl, sec-butyl or tert-butyl, in addition also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2-, 1,2,2-trimethylpropyl, heptyl, octyl, nonyl or decyl, and also, for example; trifluoromethyl or pentafluoroethyl.

A' is preferably H, methyl, ethyl, propyl, isopropyl, butyl, isobutyl, sec-butyl, tert-butyl, pentyl or hexyl.

A" is preferably methyl, ethyl, propyl, isopropyl, butyl, isobutyl, sec-butyl, tert-butyl, pentyl or hexyl.

Cycloalkyl is preferably cyclopropyl, cyclobutyl, cyclopentyl, cyclohexyl, cycloheptyl, adamantyl or 3-menthyl. Alkylene is preferably methylene, ethylene, propylene, butylene, pentylene, in addition also hexylene, heptylene, octylene, nonylene or decylene. Aralk is aralkylene and is preferably alkylenephenyl and is, for example, preferably benzyl or phenethyl.

A is very particularly preferably methyl, ethyl, propyl, isopropyl, butyl or tert-butyl.

CO—A' is alkanoyl or cycloalkanoyl and is preferably formyl, acetyl, propionyl, butyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

Preferred substituents $R^6$ for alkyl, Ar, cycloalkyl and Aralk are preferably, for example, Hal, $NO_2$, $NH_2$, NHA", such as, for example, methylamino, $NA"_2$, such as, for example, dimethylamino, methoxy, phenoxy, acyl, such as, for example, formyl or acetyl, CN, NHCOA', such as, for example, acetamido, COOA', such as, for example, COOH or methoxycarbonyl, $CONA'_2$ or $SO_2A'$, in particular, for example, F, Cl, hydroxyl, methoxy, ethoxy, amino, dimethylamino, methylthio, methylsulfinyl, methylsulfonyl or phenylsulfonyl.

In the radicals alkyl, alkylene and cycloalkyl, one, two or three methylene groups in each case can be replaced by N, O and/or S.

Ar—CO is aroyl and is preferably benzoyl or naphthoyl.

Ar is unsubstituted, preferably—as indicated—monosubstituted phenyl, specifically preferably phenyl, o-, m- or p-tolyl, o-, m- or p-ethylphenyl, o-, m- or p-propylphenyl, o-, m,- or p-isopropylphenyl, o-, m- or p-tert-butylphenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-methylthiophenyl, o-, m- or p-methylsulfinylphenyl, o-, m- or p-methylsulfonyl-phenyl, o-, m- or p-aminophenyl, o-, m- or p-methyl-aminophenyl, o-, m- or p-dimethylaminophenyl, o-, m- or p-nitrophenyl, further preferably 2,3-, 2,4-, 2,5-, 2,6-, 3,4- or 3,5-difluorophenyl, 2,3-, 2,4-, 2,5-, 2,6-3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chloro-phenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 2,3,4-, 2,3,5-, 2,3,6-, 2,4,6- or 3,4,5-trichlorophenyl, 2,4,6-tri-tert-butylphenyl, 2,5-dimethylphenyl, p-iodophenyl, 4-fluoro-3-chloro-phenyl, 4-fluoro-3,5-dimethylphenyl, 2-fluoro-4-bromo-phenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl, 2,4,6-tri-isopropylphenyl, naphthyl, 1,3-benzodioxol-5-yl, 1,4-benzodioxan-6-yl, benzothiadiazol-5-yl or benzoxadiazol-5-yl. Ar is further preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

$R^5$ is a mono- or binuclear heterocycle, preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

The heterocyclic radicals can also be partially or completely hydrogenated. $R^5$ can thus also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The heterocyclic rings mentioned can also be mono-, di- or trisubstituted by Hal, A, —CO—A, OH, CN, COOH, COOA, CONH$_2$, NO$_2$, =NH or =O.

R$^5$ is very particularly preferably 1H-imidazol-2-yl, 4,5-dihydro-1H-imidazol-2-yl, 5-oxo-4,5-dihydro-1H-imidazol-2-yl, thiazol-2-yl, 1H-benzimidazol-2-yl, 2H-pyrazol-2-yl, 1H-tetrazol-5-yl, 2-imino-imidazolidin-4-on-5-yl, 1-alkyl-1,5-dihydroimidazol-4-on-2-yl, pyridin-2-yl, pyrimidin-2-yl or 1,4,5,6-tetrahydro-pyrimidin-2-yl.

R$^1$ is particularly, for example, carboxyl, methoxycarbonyl, ethoxycarbonyl, CONH$_2$, CONHMe, CONHEt, CONMe$_2$ or CONEt$_2$. R$^1$ is very particularly preferably carboxyl or ethoxycarbonyl.

R$^2$ is preferably, for example, H, Hal, methylsulfonyl, ethylsulfonyl, propylsulfonyl, butylsulfonyl, iso-butylsulfonyl, 2,2-dimethylpropylsulfonyl, phenyl-sulfonyl or benzylsulfonyl. R$^2$ is very-particularly preferably H.

R$^3$ is preferably, for example, H$_2$N—C(=NH), H$_2$N—(C=NH)—NH, 1H-imidazol-2-ylamino, 4,5-dihydro-1H-imidazol-2-ylamino, 5-oxo-4,5-dihydro-1H-imidazol-2-ylamino, 1H-benzimidazol-2-ylamino, 2H-pyrazol-2-ylamino, 2-imino-imidazolidin-4-on-5-ylamino, 1-methyl-1,5-dihydro-imidazol-4-on-2-ylamino, pyridin-2-ylamino, pyrimidin-2-ylamino or 1,4,5,6-tetrahydropyrimidin-2-ylamino.

Accordingly, the invention relates in particular to those compounds of the formula I in which at least one of the radicals mentioned has one of the preferred meanings indicated above. Some preferred groups of compounds can be expressed by the following subformulae Ia to Ih, which correspond to the formula I and in which the radicals not described in greater detail have the meaning indicated in the formula I, but in which

| in | Ia) | R$^2$ | is H; |
|---|---|---|---|
| in | Ib) | R$^2$ | is H and |
| | | R$^1$ | is COOH or COOA; |
| in | Ic) | R$^2$ | is H, |
| | | R$^1$ | is COOH or COOA and |
| | | R$^3$ | is H$_2$N—C(=NH), H$_2$N—(C=NH)—NH, 1H-imidazol-2-ylamino, 4,5-dihydro-1H-imidazol-2-ylamino, 5-oxo-4, 5-dihydro-1H-imidazol-2-ylamino, 1H-benzimidazol-2-ylamino, 2H-pyrazol-2-ylamino, 2-iminoimidazolidin-4-on-5-ylamino, 1-methyl-1, 5-dihydroimidazol-4-on-2-yl-amino, pyridin-2-ylamino, pyrimidin-2-ylamino or 1,4,5,6-tetrahydro-pyrimidin-2-ylamino; |
| in | Id) | m | is 0 or 1; |
| in | Ie) | m | is 0 or 1 and |
| | | R$^2$ | is H; |
| in | If) | R$^2$ | is H; |
| | | R$^1$ | is COOH or COOA and |
| | | m | is 0 or 1; |
| in | Ig) | R$^2$ | is H, |
| | | R$^1$ | is COOH or COOA and |
| | | A | is methyl, ethyl, propyl, isopropyl, butyl or tert-butyl and |
| | | m | is 0 or 1; |
| in | Ih) | R$^2$ | is H, |
| | | R$^1$ | is COOH or COOA, |
| | | A | is methyl, ethyl, propyl, isopropyl, butyl or tert-butyl, |
| | | R$^3$ | is H$_2$N—C(=NH), H$_2$N—(C=NH)—NH, 1H-imidazol-2-ylamino, 4,5-dihydro-1H-imidazol-2-ylamino, 5-oxo-4, 5-dihydro-1H-imidazol-2-ylamino, 1H-benzimidazol-2-ylamino, 2H-pyrazol-2-ylamino, 2- |

-continued

| | iminoimidazolidin-4-on-5-ylamino, 1-metnyl-1,5-dihydroimidazol-4-on-2-ylamino, pyridin-2 -ylamino, pyrimidin-2-ylamino or 1,4,5,6-tetrahydropyrimidin-2-ylamino; |
|---|---|
| m | is 0 or 1 and |
| n | is 2, 3 or 4; | and their physiologically acceptable salts and solvates.

Particularly preferred groups of compounds are those below having the formulae indicated in each case Ia')

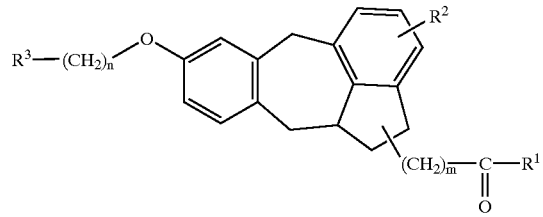

R$^2$ is H.
R$^1$ is COOH or COOA,
A is methyl, ethyl, propyl, isopropyl, butyl or tert-butyl,
R$^3$ is H$_2$N—C(=NH), H$_2$N—(C=NH)—NH, 1H-imidazol-2-ylamino, 4,5-dihydro-1H-imidazol-2-ylamino, 5-oxo-4,5-dihydro-1H-imidazol-2-ylamino, 1H-benzimidazol-2-ylamino, 2H-pyrazol-2-ylamino, 2-iminoimidazolidin-4-on-5-ylamino, 1-methyl-1,5-dihydroimidazol-4-on-2-ylamino, pyridin-2-ylamino, pyrimidin-2-ylamino or 1,4,5,6-tetrahydropyrimidin-2-ylamino;
m is 0 or 1 and
n is 2, 3 or 4;

Ia")

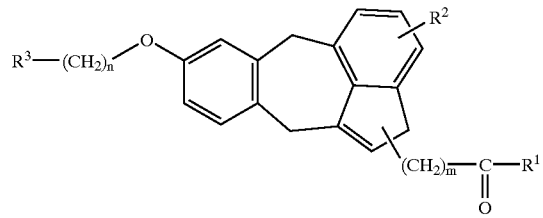

R$^2$ is H,
R$^1$ is COOH or COOA,
A is methyl, ethyl, propyl, isopropyl, butyl or tert-butyl,
R$^3$ is H$_2$N—C(=NH), H$_2$N—(C=NH)—NH, 1H-imidazol-2-ylamino, 4,5-dihydro-1H-imidazol-2-ylamino, 5-oxo-4,5-dihydro-1H-imidazol-2-ylamino, 1H-benzimidazol-2-ylamino, 2H-pyrazol-2-ylamino, 2-iminoimidazolidin-4-on-5-ylamino, 1-methyl-1,5-dihydroimidazol-4-on-2-ylamino, pyridin-2-ylamino, pyrimidin-2-ylamino or 1,4,5,6-tetrahydropyrimidin-2-ylamino;
m is 0 or 1 and
n is 2, 3 or 4;
and their physiologically acceptable salts and solvates.

The compounds of the formula I and also the starting substances for their preparation are otherwise prepared by methods known per se, such as are described in the literature (e.g. in the standard works such as Houben-Weyl, Methoden der organischen Chemie (Methods of Organic Chemistry, Georg-Thieme-Verlag, Stuttgart), namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

Compounds of the formula I can preferably be obtained by setting free compounds of the formula I from one of their functional derivatives by treating with a solvolysing or hydrogenolysing agent.

Preferred starting substances for the solvolysis or hydrogenolysis are those which otherwise correspond to the formula I, but instead of one or more free amino and/or hydroxyl groups contain corresponding protected amino and/or hydroxyl groups, preferably those which instead of an H atom which is bonded to an N atom carry an amino protective group, in particular those which instead of an HN group carry an R'—N-group, in which R' is an amino protected group, and/or those which instead of the H atom of a hydroxyl group carry a hydroxyl protective group, e.g. those which correspond to the formula I, but instead of a group —COOH carry a group —COOR", in which R" is a hydroxyl protective group. It is also possible for a number of—identical or different—protected amino and/or hydroxyl groups to be present in the molecule of the starting substance. If the protective groups present are different from one another, in many cases they can be removed selectively.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protected groups are removed after the desired reaction (or reaction sequence), their nature and size is otherwise not critical; however, those having 1–20, in particular. 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids, in particular alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl, aralkyloxycarbonyl such as CBZ ("carbobenzoxy"), 4-methoxybenzyloxycarbonyl, FMOC; arylsulfonyl such as Mtr. Preferred amino protective groups are BOC and Mtr, in addition CBZ, Fmoc, benzyl and acetyl.

The removal of the amino protective group—depending on the protective group used—takes place, for example, using strong acids, expediently using TFA or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent s possible, but not always necessary. Suitable inert solvents are preferably organic, for example carboxylic acids such as acetic acid, ethers such as tetrahydrofuran or dioxane, amides such as DMF, halogenated hydrocarbons such as dichloromethane, in addition also alcohols such as methanol, ethanol or isopropanol, and also water. Mixtures of the abovementioned solvents are additionally suitable. TFA is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°; the reaction is preferably carried out between 15 and 30° (room temperature).

The groups BOC, OBut and Mtr can preferably be removed, for example, using TFA in dichloromethane or using approximately 3 to 5N HCl in dioxane at 15–30°, the FMOC group using an approximately 5 to 50% solution of dimethylamine, diethylamine or piperidine in DMF at 15–30°.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents here are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 20–30° and 1–10 bar. Hydrogenolysis of the CBZ group takes place readily, for example, on 5 to 10% Pd/C in methanol or using ammonium formate (instead of hydrogen) on Pd/C in methanol/DMF at 20–30°.

Suitable inert solvents are, for example, hydrocarbons such as hexane, petroleum ether, benzene, toluene or xylene; chlorinated hydrocarbons such as trichloro-ethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, water or mixtures of the solvents mentioned.

It is additionally possible to convert a radical $R^1$, $R^2$ and/or $R^3$ into another radical $R^1$, $R^2$ and/or $R^3$. In particular, a carboxylic acid ester can be converted into a carboxylic acid. Thus it is possible to hydrolyse an ester of the formula I. Expediently, this is carried out by solvolysis or hydrogenolysis, as indicated above, e.g. using NaOH or KOH in dioxane/water at temperatures between 0 and 60° C., preferably between 10 and 40° C.

The conversion of a cyano group into an amidino group is carried out by reaction with, for example, hydroxylamine and subsequent reduction of the N-hydroxyamidine with hydrogen in the presence of a catalyst such as, for example, Pd/C.

It is additionally possible to replace a conventional amino protective group by hydrogen by removing the protective group solvolytically or hydrogenolytically, as described above, or by setting free an amino group protected by a conventional protective group by solvolysis or hydrogenolysis.

For the preparation of compounds of the formula I in which $R^3$ is $H_2N$—C(=NH)—NH—, an appropriate amino compound can be treated with an amidinating agent. The preferred amidinating agent is 1-amidino-3,5-dimethylpyrazole (DPFN), which is employed in particular in the form of its nitrate. The reaction is expediently carried out with addition of a base such as triethylamine or ethyldiisopropylamine in an inert solvent or solvent mixture, e.g. water/dioxane at temperatures between 0 and 120° C., preferably between 60 and 120° C.

For the preparation of an amidine of the formula I ($R^3$=—C(=NH)—$NH_2$), ammonia can be added to a nitrile of the formula I ($R^3$=CN). The addition is preferably carried out in multi-stage form, in a manner known per se, by a) converting the nitrile with $H_2S$ into a thioamide, which is converted with an alkylating agent, e.g. $CH_3I$, into the corresponding S-alkylimido thioester, which for its part reacts with $NH_3$ to give the amidine, b) converting the nitrile with an alcohol, e.g. ethanol, in the presence of HCl into the corresponding imido ester and treating this with ammonia, or c) reacting the nitrile with lithium bis(trimethylsilyl) amide and then hydrolysing the product.

Free amino groups can additionally be acylated in a customary manner using an acid chloride or anhydride or alkylated using an unsubstituted or substituted alkyl halide, expediently in an inert solvent such as dichloromethane or THF and/or in the presence of a base such as triethylamine or pyridine at temperatures between −60 and +300.

A base of the formula I can be converted into the associated acid addition salt using an acid, for example by reaction or equivalent amounts of the base and of the acid in an inert solvent such as ethanol and subsequent evaporation. Suitable acids for this reaction are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Possible salts here are in particular the sodium, potassium, magnesium, calcium and ammonium salts in addition substituted ammonium salts, e.g. the dimethyl-, diethyl- or diisopropylammonium salts, monoethanol-, diethanol- or diisopropanolammonium salts,-cyclohexyl- or dicyclohexylammonium salts, dibenzyl-ethylenediammonium salts, furthermore, for example, salts with arginine or lysine.

The compounds of the formula I contain one or more chiral centres and can therefore be present in racemic or in optically active form. Racemates obtained can be resolved into the enantiomers mechanically or chemically by methods known per se. Preferably, diastereomers are formed from the racemic mixture by reaction with an optically active resolving agent. Suitable resolving agents are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Separation of enantiomers with the aid of a column packed with an optically active resolving agent (e.g. dinitrobenzoylphenylglycine) is also advantageous; a suitable eluant is, for example, a mixture of hexane/isopropanol/acetonitrile, e.g. in the volume ratio 82:15:3.

Of course, it is also possible to obtain optically active compounds of the formula I according to the methods described above by using starting substances which are already optically active.

The invention further relates to the use of the compounds of the formula I and/or their physiologically acceptable salts for the production of pharmaceutical preparations, in particular in a non-chemical way. In this context, they can be brought into a suitable dose form together with at least one solid, liquid and/or semiliquid excipient or auxiliary and, if appropriate, in combination with one or more further active compounds.

The invention further relates to pharmaceutical preparations comprising at least one compound of the formula I and/or one of its physiologically acceptable salts.

These preparations can be used as medicaments in human or veterinary medicine. Suitable vehicles are organic or inorganic substances which are suitable for enteral (e.g. oral) or parenteral administration, topical application or for application in the form of an inhalation spray and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. Tablets, pills, coated tablets, capsules, powders, granules, syrups, juices or drops, in particular, are used for oral administration, suppositories are used for rectal administration, solutions, preferably oily or aqueous solutions, in addition suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain excipients such as lubricants, preservatives, stabilizers and/or wetting agents, emulsifiers, salts for affecting the osmotic pressure, buffer substances, colourants, flavourings and/or one or more further active compounds, e.g. one or more vitamins.

For administration as an inhalation spray, sprays can be used which contain the active compound either dissolved or suspended in a propellant or propellant mixture (e.g. $CO_2$ or chlorofluorohydrocarbons). Expediently, the active compound is used here in micronized form, it being possible for one or more additional physiologically tolerable solvents to be present, e.g. ethanol. Inhalation solutions can be administered with the aid of customary inhalers.

The invention also relates to the use of the compounds of the formula I as therapeutic active compounds.

The compounds of the formula I and their physiologically acceptable salts can be used as integrin inhibitors in the control of diseases, in particular of pathologically angiogenic disorders, thromboses, cardiac infarct, coronary heart disorders, arteriosclerosis, tumours, inflammation and infections.

As a rule, the substances according to the invention can be administered here in analogy to other known, commercially available integrin inhibitors, but in particular in analogy to the compounds described in U.S. Pat. No. 4,472,305, preferably in doses between approximately 0.05 and 500 mg, in particular between 0.5 and 100 mg per dose unit. The daily dose is preferably between approximately 0.01 and 2 mg/kg of body weight. The specific dose for each patient depends, however, on all sorts of factors, for example on the efficacy of the specific compound employed, on the age, body weight, general state of health, sex, on the diet, on the time and route of administration, and on the excretion rate, pharmaceutical combination and severity of the particular disorder to which the therapy applies. Parenteral administration is preferred.

Above and below, all temperatures are indicated in °C. In the following examples, "customary working up" means: if necessary, water is added, the mixture is adjusted, if necessary, to a pH of between 2 and 10 depending on the constitution of the final product, and extracted with ethyl acetate or dichloromethane, and the organic phase is separated off, dried over sodium sulfate and evaporated, and the residue is purified by chromatography on silica gel and/or by crystallization.

Mass spectrometry (MS): EI (electron impact ionization) $M^+$ FAB (fast atom bombardment) $(M+H)^+$ The $R_f$ values indicated were determined by thin-layer chromatography using TLC films, silica gel 60 $F_{254}$.

EXAMPLE 1

Methyl 8-[3-(pyridin-2-ylamino)propoxy]-6,11-dihydro-2H-dibenzo [cd,g]azulene-1-carboxylate A solution of 3.5 g (0.011 mol) of ethyl (3-methoxy-10,11-dihydro-5H-dibenzo[a,d]cyclohepten-10-yl)acetate in 50 ml of 1N HCl and 80 ml of dioxane is stirred at room temperature for 16 hours. After removal of the solvents, 3.0 g of (3-methoxy-10,11-dihydro-5H-dibenzo[a,d]cyclohepten-10-yl)acetic acid ("AB"), $R_f$ 0.68 (ethyl acetate) are obtained

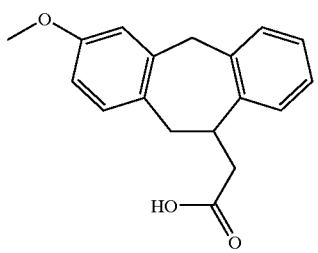

"AB"

A solution of 3.0 g of "AB" in 50 ml of thionyl chloride is treated with a few drops of DMF and stirred at 80° C. for 1 hour. After removal of the solvents, the residue is dissolved in 50 ml of dichloromethane, cooled to –10° and 1.61 g of aluminium chloride are added and the mixture is subsequently stirred at room temperature for 2 hours. It is worked up in the customary manner and purified on silica gel 60 (petroleum ether/ethyl acetate 4:1). 1.7 g of 8-methoxy-1,6,11,11a-tetrahydrodibenzo[cd,g]azulen-2-one ("AC"), $R_f$ 0.51; EI 264 are obtained

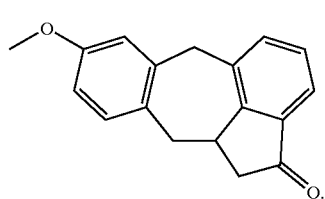

"AC"

0.64 g of NaH are added to a solution of 2.1 g of "AC" in 30 ml of THF under an argon atmosphere. After stirring for 30 minutes, 3.4 ml of dimethyl carbonate are added and the mixture is then subsequently stirred for a further 4 hours. It is worked up in the customary manner, purified on silica gel 60 (petroleum ether/ethyl acetate 4:1) and 1.8 g of methyl 8-methoxy-2-oxo-1,6,11,11a-tetrahydro-1H-dibenzo [cd,g]azulene-1-carboxylate ("AD"), $R_f$ 0.40; EI 322 are obtained

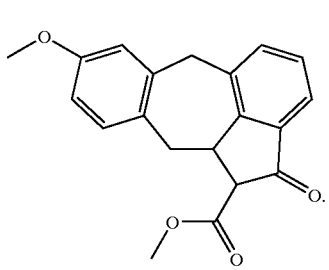

"AD"

9.3 g of ion exchanger Amberlite I and then 0.59 g of sodium borohydride are added to a solution of 1.0 g of "AD" in 155 ml of THF. The mixture is subsequently stirred at room temperature for 30 minutes. After removal of the ion exchanger and solvent, methyl 8-methoxy-2-hydroxy-1,6,11,11a-tetrahydro-1H-dibenzo-[cd,g]azulene-1-carboxylate ("AE"), $R_f$ 0.69 (petroleum ether/ethyl acetate 1:1); EI 324 is obtained

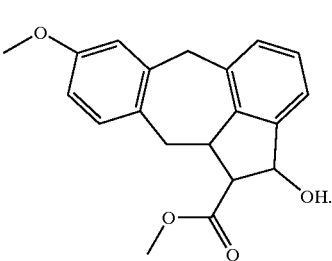

"AE"

A catalytic amount of DMAP is added to a solution of 0.3 g of "AE" in 18 ml of dichloromethane and 0.14 ml of triethylamine. The mixture is cooled in an ice bath, 0.063 ml of methanesulfonyl chloride are added and the mixture is subsequently stirred at room temperature for 14 hours. After removal of the solvents, the residue is filtered through silica gel 60 (petroleum ether/ethyl acetate 5:1). After removal of the solvents, the residue is dissolved in 50 ml of toluene, treated with 0.179 g of DBU and stirred at 800 for 16 hours. After removal of the solvent, the mixture is purified on silica gel 60 (petroleum ether/ethyl acetate 9:1). 90 mg of methyl 8-methoxy-6,11-dihydro-2H-dibenzo[cd,g]azulene-1-carboxylate ("AF"), $R_f$ 0.68 (petroleum ether/ethyl acetate 4:1) are obtained

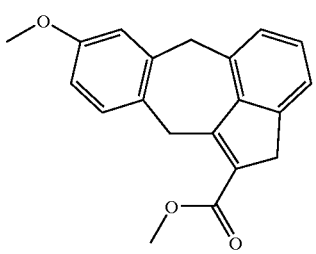

"AF"

A suspension of 0.44 g of aluminium chloride and 0.26 g of ethanethiol is cooled in an ice bath. A solution of 0.2 g of "AF" in 5 ml of dichloromethane is added. The mixture is stirred for 16 hours at room temperature, treated with 2N HCl and subsequently stirred. After customary working up, 181 mg of methyl 8-hydroxy-6,11-dihydro-2H-dibenzo[cd,g]azulene-1-carboxylate ("AG"), $R_f$ 0.368 (petroleum ether/ethyl acetate 4:1); EI 292 are obtained

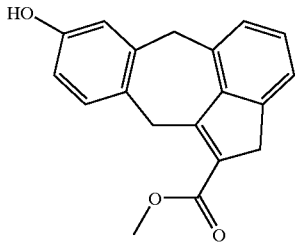

"AG"

A solution of 532 mg of 2-(3-hydroxypropylamino)-pyridine-N-oxide and 540 mg of diethyl azodicarboxylate in 10 ml of DMF is added at room temperature under an argon atmosphere to a solution of 440 mg of "AG" and 866 mg of triphenylphosphine in 20 ml of DMG. The mixture is subsequently stirred for 3 days, the solvent is separated off and the mixture is purified on silica gel 60 (ethyl acetate/methanol 9:1). 80 mg of methyl 8-[3-(1-oxypyridin-2-ylamino)propoxy]-6,11-dihydro-2H-dibenzo[cd,g]azulene-1-carboxylate ("AH"), $R_f$ 0.42 (ethyl acetate/methanol 4:1) are obtained

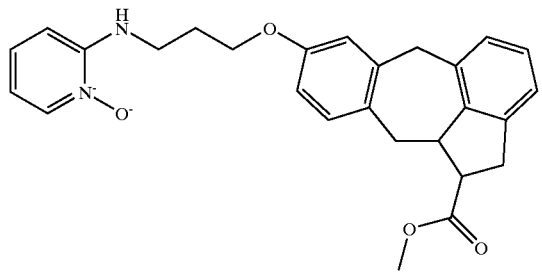

"AH"

A solution of 80 mg of "AH" and 0.063 ml of phosphorus trichloride in 15 ml of chloroform is heated under reflux for 3 hours. After customary working up, the residue is purified by means of preparative HPLC. 7.6 mg of methyl 8-[3-(pyridin-2-ylamino)propoxy]-6,11-dihydro-2H-dibenzo[cd,g]azulene-1-carboxylate ("AI"), $R_f$ 0.66 (ethyl acetate) are obtained

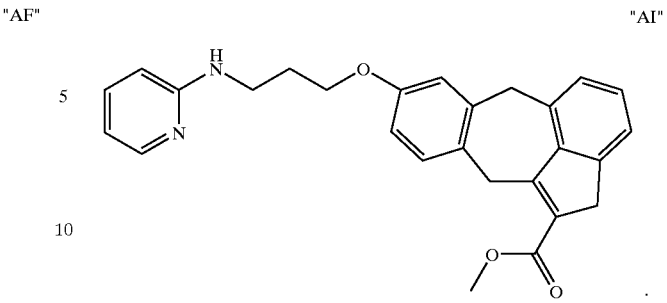

"AI"

EXAMPLE 2

8-[3-(Pyridin-2-ylamino)propoxy]-6,11-dihydro-2H-dibenzo[cd,g]azulene-1-carboxylate A solution of 7.6 mg of "AI" in 1.5 ml of dioxane is treated with 2.0 ml of 1N HCl and stirred at 110° for 16 hours. After removing the solvent, 8-[3-(pyridin-2-ylamino)propoxy]-6,11-dihydro-2H-dibenzo[cd,g]azulene-1-carboxylic acid hydrochloride, $R_f$ 0.62 (ethyl acetate/methanol 95:5+1% TEA) is obtained.

The compounds below are obtained analogously to Examples 1 and 2

8-[3-(1,4,5,6-tetrahydropyrimidin-2-ylamino)propoxy]-2,6,11,11a-tetrahydro-1H-dibenzo[cd,g]azulene-1-carboxylic acid {8-[3-(1,4,5,6-tetrahydropyrimidin-2-ylamino)propoxy]-2,6,11,11a-tetrahydro-1H-dibenzo[cd,g]azulen-2-yl}-acetic acid The following examples relate to pharmaceutical preparations:

EXAMPLE A

Injection Vials

A solution of 100 g of an active compound of the formula I and 5 g of disodium hydrogenphosphate is adjusted to pH 6.5 in 3 l of double-distilled water using 2 N hydrochloric acid, sterile filtered, dispensed into injection vials, lyophilized under sterile conditions and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The solution is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F

Coated Tablets

Tablets are pressed analogously to Example E and are then coated with a coating of sucrose, potato starch, talc, tragacanth and colourant in a customary manner.

EXAMPLE G

Capsules 2 kg of active compound of the formula I are filled into hard gelatin capsules in a customary manner such that each capsule contains 20 mg of the active compound.

EXAMPLE H

Ampoules

A solution of 1 kg of active compound of the formula I in 60 l of double-distilled water is sterile filtered, dispensed into ampoules, lyophilized under sterile conditions and aseptically sealed. Each ampoule contains 10 mg of active compound.

EXAMPLE I

Inhalation Spray 14 g of active compound of the formula I are dissolved in 10 l of isotonic NaCl solution and the solution is filled into commercially available spray containers having a pump mechanism. The solution can be sprayed into the mouth or nose. One burst of spray (approximately 0.1 ml) corresponds to a dose of approximately 0.14 mg.

What is claimed is:

1. Compounds of the formula I

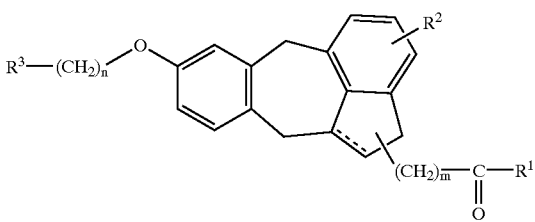

in which $R^1$ is $OR_4$, $NHR^4$ or $NA''_2$, $R^2$ is H, Hal, $NO_2$, $NHR^4$, $NA''_2$, $OR^4$, $SO_3R^4$, $SO_2R^4$ or $SR^4$, $R^3$ is $NH_2$, $H_2N-C(=NH)$ or $H_2N-(C=NH)-NH$, where the primary amino groups are optionally protected with an amino protective group or $R^5-NH-$, $R^4$ is H, A, Ar, or Aralk, $R^5$ is a mono- or binuclear heterocycle having 1 to 4 N, O and/or S atoms, which can be unsubstituted or mono-, di- or trisubstituted by Hal, A'', $-CO-A$, OA', CN, COOA', $CONH_2$, $NO_2$, =NH or =O, A is alkyl having 1–15 C atoms or cycloalkyl having 3–15 C atoms, which is unsubstituted or mono-, di- or trisubstituted by $R^6$, and in which one, two or three methylene groups can be replaced by N, O and/or S, $R^6$ is Hal, $NO_2$, NHA', $NA''_2$, OA', phenoxy, CO—A', $SO_3A'$, CN, NHCOA', COOA', $CONA'_2$, or $SO_2A'$, A' is H or alkyl having 1–6 C atoms, A'' is alkyl having 1–6 C atoms, Ar is a mono- or binuclear aromatic ring system, which is unsubstituted or mono-, di- or trisubstituted by alkyl having 1–6 C atoms and/or an $R^6$-substituted mono- or binuclear aromatic ring system having 0, 1, 2, 3 or 4 N, O and/or S atoms, Aralk is a aralkylene having 7–14 C atoms, which is unsubstituted or mono-, di- or trisubstituted by $R^6$ and in which one, two or three methylene groups can be replaced by N, O and/or S, Hal is F, Cl, Br, or I, m, n in each case independently of one another are 0, 1, 2, 3, or 4, and their physiologically acceptable salts and solvates.

2. Enantiomers or diastereomers of the compounds of the formula I according to claim 1.

3. Compounds of the formula I according to claim 1 a) 8-[3-(pyridin-2-ylamino)propoxy]-6,11-dihydro-2H-dibenzo[cd, g]azulene-1-carboxylic acid;

b) 8-[3-(1,4,5,6-tetrahydropyrimidin-2-ylamino)propoxy]-2,6,11,11a-tetrahydro-1H-dibenzo[cd,g]azulene-1-carboxylic acid;

c) {8-[3-(1,4,5,6-tetrahydropyrimidin-2-ylamino)propoxy]-2,6,11,11a-tetrahydro-1H-dibenzo[cd,g]azulene-2-yl}acetic acid;

and their physiologically acceptable salts and solvates.

4. Process for the preparation of compounds of the formula I according to claim 1, and of their salts and solvates, characterized in that a) a compound of the formula I is set free from one of its functional derivatives by treating with a solvolysing or hydrogenolysing agent, or b) a radical $R^1$, $R^2$, and/or $R^3$ is converted into another radical, $R^1$, $R^2$, and/or $R^3$ by, i) converting an amino group into a guanidino group by reaction with an amidinating agent, ii) hydrolysing an ester, iii) reducing a carboxylic acid to an alcohol, or iv) converting a hydroxyamidine into an amidine by hydrogenation or c) a base or acid of the formula I is converted into one of its salts.

5. Compounds of the formula I according to claim 1 and their physiologically acceptable salts and solvates as GPIIb/IIIa antagonists for the control of thromboses, cardiac infarct, coronary heart disorders and arteriosclerosis.

6. Compounds of the formula I according to claim 1 and their physiologically acceptable salts and solvates as $α_v$ integrin inhibitors for the control of pathologically angiogenic disorders, thromboses, cardiac infarct, coronary heart disorders, arteriosclerosis, tumours, osteoporosis and rheumatoid arthritis.

7. A pharmaceutical composition characterized in that it contains at least one compound of the formula I according to claim 1 and/or one of its physiologically acceptable salts or solvates.

8. A process for the production of a pharmaceutical composition characterized in that a compound of formula I according to claim 1 and/or one of its physiologically acceptable salts or solvates is brought into a suitable dose form together with at least one solid, liquid or semi-liquid vehicle or excipient.

9. A method for treatment of a disease or condition affected by $α_v$ integrin inhibition which comprises administering an α_v integrin inhibition effective amount of a compound of the formula I of claim 1 or physiologically acceptable salt or solvate thereof.

10. The method of claim 9, wherein the disease or condition is cancer, a tumor-induced angiogenic disease, oncoses, osteoporosis, an osteolytic disorder, angiogenesis, thromboses, cardiac infarct, coronary heart disorder, arteriosclerosis or rheumatoid arthritis.

11. Compounds of claim 1, wherein:

Aralk is benzyl or phenethyl,

A is methyl, ethyl, propyl, isopropyl, butyl or tert-butyl,

Ar is unsubstituted or mono-substituted phenyl, and $R^5$ is 1H-imidazol-2-yl, 4,5-dihydro-1H-imidazol-2-yl, 5-oxo-4,5-dihydro-1H-imidazol-2-yl, thiazol-2-yl, 1H-benzimidazol-2-yl, 2H-pyrazol-2-yl, 1H-tetrazol-5-yl, 2-imino-imidazolin-4-on-5-yl, 1-alkyl-1,5-dihydroimidazol-4-on-2-yl, pyridin-2-yl, pyrimidin-2-yl or 1,4,5,6-tetrahydro-pyrimidin-2-yl.

12. Compounds of claim 1, wherein $R^2$ is H.

13. Compounds of claim 1, wherein $R^2$ is H, $R^1$ is $OR^4$ and $R^4$ is H or A.

14. Compounds of claim 1, wherein $R^2$ is H, $R^1$ is $OR^4$, $R^4$ is H or A and $R^3$ is $H_2N-C(=NH)$, $H_2N-(C=NH)-NH$, 1H-imidazol-2-ylamino, 4,5dihydro-1H-imidazol-2-ylamino, 5-oxo-4,5-dihydro-1H-imidazol-2-ylamino, 1H-benzimidazol-2-ylamino, 2H-pyrazol-2-ylamino, 1-methyl-1,5-dihydroimidazol-4-on-2-yl-amino, pyridin-2-ylamino, pyrimidin-2-ylamino or 1,4,5,6-tetrahydro-pyrimidin-2-ylamino.

15. Compounds of claim 1, wherein m is 0 or 1.

16. Compounds of claim 1, wherein m is 0 or 1 and $R^2$ is H.

17. Compounds of claim 1, wherein $R^2$ is H; $R^1$ is $OR^4$, $R^4$ is H or A and m is 0 or 1.

18. Compounds of claim 1, wherein $R^2$ is H, $R^1$ is $OR^4$, $R^4$ is H or A and A is methyl, ethyl, propyl, isopropyl, butyl or tert-butyl and m is 0 or 1.

19. Compounds of claim 1, wherein $R^2$ is H, $R^1$ is $OR^4$, $R^4$ is H or A, A is methyl, ethyl, propyl, isopropyl, butyl or tert-butyl, $R^3$ is $H_2N-C(=NH)$, $H_2N-(C=NH)$, $H_2N-(C=NH)-NH$, 1H-imidazol-2-ylamino, 4,5dihydro-1H-imidazol-2-ylamino, 5-oxo4,5-dihydro-1H-imidazol-2-ylamino, 1H-benzimidazol-2-ylamino, 2H-pyrazol-2-ylamino, 2-iminoimidazolidin-4-on-5-ylamino, 1-methyl-1,5-dihydroimidazol-4-on-2-ylamino, pyridin-2-ylamino, pyrimidin-2-ylamino or 1,4,5,6,-tetrahydropyrimidin-2-ylamino;

m is 0 or 1 and n is 2, 3 or 4.

20. Compounds of claim 1, wherein the amino protective group, if present, is an unsubstituted or substituted acyl, aralkoxymethyl or aralkyl group.

21. Compounds of claim 20, wherein the amino protective group, if present, is BOC, Mtr, CBZ, Fmoc, benzyl or acetyl.

* * * * *

UNITED STATES PATENT AND TRADEMARK OFFICE
CERTIFICATE OF CORRECTION

PATENT NO.     : 6,521,646 B1
DATED          : February 18, 2003
INVENTOR(S)    : Wolfgang Stahle et al.

It is certified that error appears in the above-identified patent and that said Letters Patent is hereby corrected as shown below:

Column 17,
Line 50, reads "$OR_4$" should read -- $OR^4$ --

Column 19,
Line 25, reads "4,5 dihyydro" should read -- 4,5-dihydro --

Column 20,
Line 13, reads "4,5 dihydro" should read -- 4,5-dihydro --.
Line 14, reads "5-oxo4,5-" should read -- 5-oxo-4,5- --

Signed and Sealed this

Tenth Day of August, 2004

JON W. DUDAS
*Acting Director of the United States Patent and Trademark Office*